(12) United States Patent
Hjälm

(10) Patent No.: US 7,208,305 B2
(45) Date of Patent: Apr. 24, 2007

(54) VARIANTS OF THE α1 SUBUNIT OF HUMAN AMPK

(75) Inventor: Göran Hjälm, Uppsala (SE)

(73) Assignee: Arexis AB, Gothenburg (SE)

( * ) Notice: Subject to any disclaimer, the term of this patent is extended or adjusted under 35 U.S.C. 154(b) by 0 days.

(21) Appl. No.: 10/503,038

(22) PCT Filed: Jan. 31, 2003

(86) PCT No.: PCT/IB03/00807

§ 371 (c)(1),
(2), (4) Date: Feb. 23, 2005

(87) PCT Pub. No.: WO03/064466

PCT Pub. Date: Aug. 7, 2003

(65) Prior Publication Data

US 2005/0170349 A1 Aug. 4, 2005

Related U.S. Application Data

(60) Provisional application No. 60/353,406, filed on Feb. 1, 2002.

(51) Int. Cl.
| | |
|---|---|
| *C12N 9/12* | (2006.01) |
| *C12N 15/70* | (2006.01) |
| *C12Q 1/68* | (2006.01) |
| *C12P 21/06* | (2006.01) |
| *C07H 21/02* | (2006.01) |
| *C07H 21/04* | (2006.01) |

(52) U.S. Cl. .................. 435/194; 435/6; 435/69.1; 435/320.1; 536/23.1; 536/23.2

(58) Field of Classification Search .............. 435/194; 536/23.2
See application file for complete search history.

(56) References Cited

U.S. PATENT DOCUMENTS

| 4,946,778 A | 8/1990 | Ladner et al. |
| 5,846,720 A | 12/1998 | Foulkes et al. |

FOREIGN PATENT DOCUMENTS

| WO | WO 97/25341 | 7/1997 |

OTHER PUBLICATIONS

Ota et al. (GenBank Accession No. AK024252, created Sep. 30, 2000) *Homo sapiens* cDNA FLJ14190 fis, clone NT2RP2006354, moderately similar to 5'-AMP-activated protein kinase, catalytic alpha-1 chain (EC 2.7.1.-).*
Verhoeven et al. "The AMP-activated protein kinase gene is highly expressed in rat skeletal muscle: Alternative splicing and tissue distribution of the mRNA", Eur. J. Biochem. 228: 236-243, 1995.*
GenBank Accession No. AB022017 dated Jan. 8, 1999, 2 pages.
GenBank Accession No. AAH48980 dated Apr. 22, 2003, 2 pages.
GenBank Accession No. NM_006251 dated Oct. 18, 2005, 8 pages.

Cheung et al., "Characterization of AMP-activated protein kinase γ-subunit isoforms and their role in AMP binding," *Biochem. J.*, 2000, 346:659-669.
Cole et al., *Monoclonal Antibodies and Cancer Therapy*; 1983, Alan R. Liss, Inc., pp. 77-96.
Collins, "Generation and initial analysis of more than 15,000 full-length human and mouse cDNA sequences," *Proc. Natl. Acad. Sci. USA*, 2002, 99(26):16899-16903.
Cote et al., "Generation of human monoclonal antibodies reactive with cellular antigens," *Proc. Natl. Acad. Sci. USA*, 1983, 80:2026-2030.
Davies et al., "Tissue distribution of the AMP-activated protein kinase, and lack of activation by cyclic-AMP-dependent protein kinase, studied using a specific and sensitive peptide assay," *Eur. J. Biochem.*, 1989, 186:123-128.
Engh and Bossemeyer, "The Protein Kinase Activity Modulation Sites: Mechanisms for Cellular Regulation—Targets for Therapeutic Intervention," *Advan. Enzyme Regul.*, 2001, 41:121-149.
Hardie and Carling, "The AMP-activated protein kinase. Fuel gauge of the mammalian cell?" *Eur. J. Biochem.*, 1997, 246:259-273.
Hardie et al., "The AMP-Activated/SNF1 Protein Kinase Subfamily: Metabolic Sensors of the Eukaryotic Cell?" *Annu. Rev. Biochem.*, 1998, 67:821-855.
Hardie and Hawley, "AMP-activated protein kinase: the energy charge hypothesis revisited," *BioEssays*, 2001, 23:1112-1119.
Holmes et al., "Chronic activation of 5'-AMP-activated protein kinase increases GLUT-4, hexokinase, and glycogen in muscle," *J. Appl. Physiol.*, 1999, 87(5):1990-1995.
Huse et al., "Generation of a Large Combinatorial Library of the Immunoglobulin Repertoire in Phage Lambda," *Science*, 1989, 246:1275-1281.
International Human Genome Sequencing Consortium, *Nature*, 2001, 409:860-921.
Köhler and Milstein, "Continuous cultures of fused cells secreting antibody of predefined specificity," *Nature*, 1975, 256:495-497.
Kozbor and Roder, "The production of monoclonal antibodies from human lymphocytes," *Immunology Today*, 1983, 4(3):72-79.
Michell et al., "Isoform-specific Purification and Substrate Specificity of the 5'-AMP-activated Protein Kinase," *J. Biol. Chem.*, 1996, 271(45):28445-28450.
Winder and Hardie, "AMP-activated protein kinase, a metabolic master switch: possible roles in Type 2 diabetes," *Am. J. Physiol.*, 1999, 277:E1-E10.
Zhou et al., "Role of AMP-activated protein kinase in mechanism of metformin action," *J. Clin. Invest.*, 2001, 108(8):1167-1174.

* cited by examiner

*Primary Examiner*—Ponnathapura Achutamurthy
*Assistant Examiner*—Iqbal Chowdhury
(74) *Attorney, Agent, or Firm*—Fish & Richardson P.C.

(57) ABSTRACT

Variants of the α subunit of AMP-activated kinase (AMPK), nucleic acids encoding such variants, and methods for their use are provided. The AMPK variants include splice variants that have an additional exon in the AMPK mRNA, and thus have an additional 15 amino acid residues in the encoded polypeptide. The AMPK variants can, for example, have at least 75% identity to the amino acid sequence of SEQ ID NO:4, and can contain an amino acid sequence having at least 75% identity to the amino acid sequence of SEQ ID NO:2.

3 Claims, No Drawings

VARIANTS OF THE α1 SUBUNIT OF HUMAN AMPK

CROSS-REFERENCE TO RELATED APPLICATIONS

This application is a National Stage application under 35 U.S.C. § 371 and claims benefit under 35 U.S.C. § 119(a) of International Application No. PCT/IB03/00807 having an International Filing Date of Jan. 31, 2003, which claims the benefit of priority of U.S. Provisional Application Ser. No. 60/353,406 having a filing date of Feb. 1, 2002.

TECHNICAL FIELD

The invention relates to protein kinases, and more particularly to variants of the alpha subunit of the human AMP-activated protein kinase.

BACKGROUND

The AMP-activated protein kinase (AMPK) acts as an intracellular metabolic sensor in a variety of cells, where it monitors and responds to variations in the AMP:ATP ratio (Hardie et al., *Annu. Rev. Biochem.* 67:821–855, 1998). Upon activation of AMPK, the enzyme phosphorylates a number of protein substrates to decrease further ATP usage by the cell. AMPK is a heterotrimeric complex consisting of a catalytic subunit (α) and two associated subunits (β and γ). Both the β and γ subunits are required for optimal activity of the α catalytic subunit. The AMPK complex is evolutionarily conserved and also can be found in yeast and plants. Mammalian AMPK is composed of different isoforms of subunits: α1, α2, β1, β2, γ1, γ2, and γ3 (Hardie and Hawley, *BioEssays* 23:1112–1119, 2001). Different combinations of isoform subunits are activated differently in vivo, and most likely also differ in substrate utilization. AMPK activity is found in several tissues, including liver, kidney, muscle, lung, and brain (Cheung et al., *Biochem. J.* 346: 659–669, 2000).

AMPK is recognized as a major regulator of lipid biosynthetic pathways due to its role in the phosphorylation and inactivation of key enzymes such as acetyl-CoA carboxylase (Hardie and Carling, *Eur. J. Biochem.* 246:259–273, 1997). More recent work has suggested that AMPK has a wider role in metabolic regulation (Winder and Hardie, *Am. J. Physiol.* 277:E1–10, 1999); this includes fatty acid oxidation, muscle glucose uptake, expression of cAMP-stimulated gluconeogenic genes such as PEPCK and G6Pase, and expression of glucose-stimulated genes associated with hepatic lipogenesis, including fatty acid synthase, Spot-14, and L-type pyruvate kinase. Chronic activation of AMPK also can induce the expression of muscle hexokinase and glucose transporters (Glut4), mimicking the effects of extensive exercise training (Holmes et al. *J. Appl. Physiol.* 87:1990–1995, 1999). The activation of AMPK thus might be a good approach to treat type 2 diabetes; this hypothesis is supported by the finding that AMPK is the target for metformin, a drug widely used to treat type 2 diabetes (Zhou et al. *J. Clin. Invest.* 108:1167–1174, 2001).

SUMMARY

The invention is based on the identification of variants of the α1 subunit of human AMPK, including splice variants that result in inclusion of an additional exon in the AMPK mRNA and an additional 15 amino acid residues in the encoded polypeptide. Such a polypeptide can regulate the activity of the AMPK trimer or alter the substrate specificity of the kinase.

In one aspect, the invention features a purified polypeptide that includes a splice variant of the α1 subunit of human AMPK. The purified polypeptide can contain the amino acid sequence of SEQ ID NO:2, or can contain an amino acid sequence having at least 75% identity to the amino acid sequence of SEQ ID NO:2. The purified polypeptide can have the amino acid sequence of SEQ ID NO:4.

The invention also features an isolated nucleic acid encoding a polypeptide, wherein the polypeptide is a splice variant of the α1 subunit of human AMPK. The isolated nucleic acid can contain a nucleotide sequence at least 75% identical to the nucleotide sequence of SEQ ID NO:1. The isolated nucleic acid sequence can have the nucleotide sequence of SEQ ID NO:3. The invention also features an expression construct containing such nucleic acids.

In anther aspect, the invention features a method for identifying an agent capable of modulating the activity of a polypeptide, wherein the polypeptide is a splice variant of the α1 subunit of human AMPK. The method can include contacting a candidate compound with the polypeptide or with a plurality of cells expressing the polypeptide, measuring the effect of the candidate compound on the activity of the polypeptide, and identifying the candidate compound as an agent capable of modulating the activity of the polypeptide if the activity is increased or decreased in the presence of the compound.

The invention also features a method for identifying an agent capable of modulating the activation of a polypeptide, wherein the polypeptide is a splice variant of the α1 subunit of human AMPK. The method can include contacting a candidate compound with the polypeptide or with a plurality of cells expressing the polypeptide, measuring the effect of the candidate compound on the activation of the polypeptide, and identifying the candidate compound as an agent capable of modulating the activation of the polypeptide if the activation is increased or decreased in the presence of the candidate compound.

The invention features a method for identifying an agent capable of modulating the amount of a polypeptide produced by a cell, where the polypeptide is a splice variant of the α1 subunit of human AMPK. The method can involve contacting a candidate compound with a plurality of cells expressing the polypeptide, measuring the effect of the candidate compound on the amount of the polypeptide produced by the cells, and identifying the candidate compound as an agent capable of modulating the amount of the polypeptide produced by the cell if the amount is increased or decreased in the presence of the candidate compound.

In yet another aspect, the invention features an isolated antibody having specific binding affinity for a polypeptide, where the polypeptide is a splice variant of the α1 subunit of human AMPK.

The invention also features an isolated nucleic acid probe that specifically hybridizes to a nucleic acid encoding a splice variant of the α1 subunit of human AMPK or the complement of the nucleic acid. The nucleic acid probe can specifically hybridize to the nucleic acid sequence of SEQ ID NO:1 or a sequence complementary thereto.

The invention also features a method for specifically detecting the presence of a polypeptide in a sample, where the polypeptide is a splice variant of the α1 subunit of human AMPK. The method involves contacting the sample with an antibody described above.

The invention also features a method for specifically detecting the presence of an AMPK heterotrimer complex in a biological sample containing a polypeptide, where the polypeptide is a splice variant of the α1 subunit of human AMPK. The method can include contacting the biological sample with an antibody described above.

The invention also features a method for specifically detecting the presence of a nucleic acid encoding a splice variant of the α1 subunit of human AMPK. The method can involve contacting a biological sample with a nucleic acid probe described above.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying description below. Other features, objects, and advantages of the invention will be apparent from the description and, from the claims.

DETAILED DESCRIPTION

In general, the invention provides polypeptides that are splice variants of the α1 subunit of AMPK and nucleic acids encoding such polypeptides. As described herein, a polypeptide splice variant of the α1 subunit of AMPK contains an additional 15 amino acid residues and can result in an AMPK trimer having a different structural surface than an AMPK trimer containing an α1 subunit that lacks these extra amino acid residues. This may have a direct effect on substrate binding to AMPK. For example, a protein that normally functions as a substrate for AMPK may not retain the ability to function as a substrate, possibly because new interactions prevent the substrate from fitting properly into the substrate pocket of the kinase. Since AMPK is known to have different substrates that are involved in different signaling and metabolic pathways, the presence of a variant of the α1 subunit could alter the activity of the kinase in different signaling and metabolic pathways.

A structural model of the core domain of another kinase (Engh and Bossemeyer, *Advan. Enzyme Regul.* 41:124, 2001) indicates that the substrate pocket of a kinase consists of two parts, a small substrate pocket and a large substrate pocket. The small substrate pocket typically is where the substrate amino acid residue to be phosphorylated interacts with the kinase. The large substrate pocket is defined as the bigger part of the cleft between the two subdomains of a kinase core domain, where the rest of the substrate protein interacts with the kinase during a phosphorylation event or where the substrate protein would be in close proximity to the kinase. Without being bound by a particular mechanism, the polypeptide sequence encoded by the additional exon identified herein can lie on one side of the larger substrate pocket of the kinase cleft. More specifically, this polypeptide sequence can be found between alpha helix D and alpha helix E (as defined in Engh and Bossemeyer, supra). This could either extend the two existing helixes or protrude in an enlarged loop linking the two helixes. The function of polypeptide sequence encoded by the additional exon could, in an AMPK trimer complex: (i) alter the substrate specificity of the kinase, and/or (ii) have a regulatory effect on the activity of the kinase.

The presence of a variant of the α1 subunit in an AMPK kinase trimer also could potentiate the use of a new substrate. The presence of a variant of the α1 subunit could provide the structural requirements needed for a protein that is otherwise not a substrate for AMPK to be able to bind to the kinase and thus function as a substrate.

Variants of the α1 subunit of human AMPK could have a role in regulation of the activity of the AMPK trimer. For example, an α1 subunit variant could affect the ability of AMP to activate the kinase, by directly or indirectly changing the sensitivity for the kinase to AMP. AMPK is activated by phosphorylation of an upstream AMPK-kinase (AMPKK) and the presence of a variant of the α1 subunit could affect, by steric constraints, the ability of AMPKK to phosphorylate AMPK. Furthermore, the presence of a α1 subunit variant could change, also by steric considerations, the regulation of AMPK activation by dephosphorylation.

Polypeptides

The present invention provides polypeptides that are variants of the α1 subunit of human AMPK. A "polypeptide" refers to a chain of amino acid residues, regardless of post-translational modification (e.g., phosphorylation or glycosylation). As used herein, "variants of the α1 subunit of human AMPK" have an amino acid sequence that differs from the amino acid sequence of the wild type human AMPK α1 subunit (see GenBank Accession No. NM_006251). Variants can result from, for example, a substitution, deletion, or insertion within the wild type amino acid sequence.

A variant can be, for example, a naturally occurring splice variant of the human AMPK α1 subunit. In one embodiment, a splice variant includes an amino acid sequence encoded by additional exon sequences of the α1 subunit of human AMPK. The additional exon sequence can be located, for example, between exon 3 and exon 4 of the gene encoding the α1 subunit of human AMPK. The additional exon sequence can be the sequence set forth in SEQ ID NO:1.

The present invention further provides variants of the α1 subunit of human AMPK containing the amino acid sequence shown in SEQ ID NO:2 or an amino acid sequence that is at least 75% identical (e.g., at least 80% identical, at least 90% identical, or at least 95% identical), to a polypeptide containing the amino acid sequence of SEQ ID NO:2. The variant can have, for example, the amino acid sequence shown in SEQ ID NO:4.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., percent identity=number of identical positions/total number of positions (e.g., overlapping positions)×100). In one embodiment, the two sequences are the same length.

To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (world wide web at fr.com/blast) or the U.S. government's National Center for Biotechnology Information web site (world wide web at ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q −1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 50 nucleotide target sequence is compared to the sequence set forth in SEQ ID NO:1, (2) the Bl2seq program presents 45 nucleotides from the target sequence aligned with a region of the sequence set forth in SEQ ID NO:1 where the first and last nucleotides of that 45 nucleotide region are matches, and (3) the number of matches over those 45 aligned nucleotides is 40, then the 50 nucleotide target sequence contains a length of 45 and a percent identity over that length of 89 (i.e., 40/45×100=89).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Antibodies

The invention also provides antibodies that have specific binding affinity for a polypeptide variant of the $\alpha1$ subunit of human AMPK. "Antibody" or "antibodies" includes intact molecules as well as fragments thereof that are capable of binding to an epitope of an AMPK $\alpha1$ subunit. The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids. The terms "antibody" and "antibodies" include polyclonal antibodies, monoclonal antibodies, humanized or chimeric antibodies, single chain Fv antibody fragments, Fab fragments, and $F(ab)_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful.

In general, an AMPK $\alpha1$ polypeptide is produced, for example, by chemical synthesis or by purification of the native protein and then used to immunize animals. Various host animals including, for example, rabbits, chickens, mice, guinea pigs, and rats, can be immunized by injection of the protein of interest. Depending on the host species, adjuvants can be used to increase the immunological response and include Freund's adjuvant (complete and/or incomplete), mineral gels such as aluminum hydroxide, surface-active substances such as lysolecithin, pluronic polyols, polyanions, peptides, oil emulsions, keyhole limpet hemocyanin, and dinitrophenol. Polyclonal antibodies are contained in the sera of the immunized animals. Monoclonal antibodies can be prepared using standard hybridoma technology. In particular, monoclonal antibodies can be obtained by any technique that provides for the production of antibody molecules by continuous cell lines in culture as described, for example, by Kohler et al. (1975) *Nature* 256:495–497, the human B-cell hybridoma technique of Kosbor et al. (1983) *Immunology Today* 4:72, and Cote et al. (1983) *Proc. Natl. Acad. Sci. USA* 80:2026–2030, and the EBV-hybridoma technique of Cole et al., *Monoclonal Antibodies and Cancer Therapy*, Alan R. Liss, Inc. pp. 77–96 (1983). Such antibodies can be of any immunoglobulin class including IgM, IgG, IgE, IgA, IgD, and any subclass thereof. The hybridoma producing the monoclonal antibodies of the invention can be cultivated in vitro or in vivo.

A chimeric antibody is a molecule in which different portions are derived from different animal species, such as those having a variable region derived from a mouse monoclonal antibody and a human immunoglobulin constant region. Chimeric antibodies can be produced through standard techniques.

Antibody fragments that have specific binding affinity for an AMPK $\alpha1$ subunit polypeptide can be generated by known techniques. Such antibody fragments include, but are not limited to, $F(ab')_2$ fragments that can be produced by pepsin digestion of an antibody molecule, and Fab fragments that can be generated by deducing the disulfide bridges of $F(ab')_2$ fragments. Alternatively, Fab expression libraries can be constructed. See, for example, Huse et al. (1989) *Science* 246:1275–1281. Single chain Fv antibody fragments are formed by linking the heavy and light chain fragments of the Fv region via an amino acid bridge (e.g., 15 to 18 amino acids), resulting in a single chain polypeptide.

Single chain Fv antibody fragments can be produced through standard techniques, such as those disclosed in U.S. Pat. No. 4,946,778.

Once produced, antibodies or fragments thereof can be tested for recognition of an AMPK α1 subunit by standard immunoassay methods including, for example, enzyme-linked immunosorbent assay (ELISA) or radioimmunoassay (RIA). See *Short Protocols in Molecular Biology*, eds. Ausubel et al., Green Publishing Associates and John Wiley & Sons (1992). Suitable antibodies typically have equal binding affinities for recombinant and native proteins.

Antibodies that have specific binding affinity for an AMPK α1 subunit variant can be used to detect variants of the α1 subunit of human AMPK in a biological sample. As used herein, a biological sample contains cells or cellular material, and can include, for example, urine, blood, cerebrospinal fluid, pleural fluid, sputum, peritoneal fluid, bladder washings, secretions, oral washings, tissue samples, touch preps, or fine-needle aspirates. Methods for detecting α1 subunit variants include contacting such a sample with an antibody of the invention. The variant of the α1 subunit can be, present in an AMPK heterotrimer complex.

Nucleic Acids

The present invention further provides isolated nucleic acid molecules encoding variants of the α1 subunit of human AMPK. Nucleic acids of the invention can contain nucleotide sequences that are at least 75% identical (e.g., at least 80% identical, at least 90% identical, or at least 95% identical), to the nucleotide sequence of SEQ ID NO:1. The nucleotide sequence of an isolated nucleic acid sequence may be, for example, the nucleotide sequence shown in SEQ ID NO:3.

The invention also provides vectors containing nucleic acid sequences encoding variants of the α1 subunit of human AMPK. As used herein, a "vector" is a replicon, such as a plasmid, phage, or cosmid, into which another DNA segment can be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

An expression vector containing a nucleic acid that encodes a variant of the human AMPK α1 subunit can be introduced into host cells by any of a number of techniques including, for example, calcium phosphate transformation, DEAE-dextran transformation, cationic lipid mediated lipofection, electroporation, or infection.

The α1 subunit can be expressed in a variety of hosts such as bacteria, plant cells, insect cells, fungal cells, and human and animal cells. Eukaryotic recombinant host cells are particularly useful. Nonlimiting examples include yeast, mammalian cells including cell lines of human, bovine, porcine, monkey, and rodent origin, and insect cells including *Drosophila* and silkworm derived cell lines. Examples of cell lines derived from mammalian species that are commercially available include: L cells L-M(TK-) (ATCC CCL 1.3), L cells L-M (ATCC CCL 1.2), HEK 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The invention further provides nucleic acid probes that can specifically hybridize to a nucleic acid encoding a variant of the α1 subunit of human AMPK or to the complement of the nucleic acid. Nucleic acid probes that specifically hybridize to the nucleotide sequences of SEQ ID NO:1 and SEQ ID NO:3, or sequences complementary thereto are particularly useful. Such nucleic acid probes are useful, for example, for amplifying and/or detecting a nucleic acid encoding a polypeptide of the invention.

"Specific hybridization" of a nucleic acid probe refers to a nucleic acid that hybridizes only to nucleic acids encoding variants of the α1 subunit of human AMPK, or the complements thereof, without hybridizing to nucleic acids encoding related polypeptides. Such hybridization typically is carried out under stringent hybridization conditions. The term "stringent" when used in conjunction with hybridization conditions is as defined in the art, i.e., 15–20° C. under the melting point Tm. Preferably the conditions are "highly stringent," i.e., 5–10° C. under the melting point Tm. High stringency conditions can include the use of low ionic strength buffer and a high temperature for washing, for example, 0.015 M NaCl/0.0015 M sodium citrate (0.1× SSC), 0.1% sodium dodecyl sulfate (SDS) at 65° C. Alternatively, denaturing agents such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Defining appropriate hybridization conditions is within the skill of the art. See, e.g., *Molecular Cloning: A Laboratory Manual*, 3rd ed., Sambrook et al. eds., Cold Spring Harbor Laboratory Press, 2001; *DNA Cloning: A practical Approach*, Glover & Hames eds., Oxford University Press, 1996; and *Nucleic Acid Hybridization: Essential techniques*, Ross ed. Wiley, 1998.

Methods

The invention provides methods for identifying a therapeutic agent capable of modulating the activity of a polypeptide, where the polypeptide is a variant of the α1 subunit of human AMPK. Such methods can include: (i) contacting a candidate compound with such a polypeptide or a plurality of cells expressing such a polypeptide; and (ii) measuring the effect of the candidate compound on the activity of the polypeptide. Modulating the activity of a variant of the α1 subunit of human AMPK can be achieved by, for example, modulating the level of phosphorylation, substrate specificity, AMP activation, substrate affinity, or resistance to protein phosphorylases. Modulating the activity of a variant of the α1 subunit of human AMPK can occur by either stimulation or inhibition. Agents that can stimulate the activity of a variant of the α1 subunit of human AMPK are particularly useful.

Methods of the invention also can be used to identify a therapeutic agent capable of modulating the activation of a variant of the α1 subunit of human AMPK according to the invention. AMPK can be allosterically activated by AMP, or activated by phosphorylation (e.g., in the activation loop of the α1 subunit). Thus, modulation of the activation of a variant of the α1 subunit of human AMPK can be achieved through, for example, modulating the level of phosphorylation, AMP activation, or resistance to protein phosphorylases. Methods for identifying such therapeutic agents can include:

(i) contacting a candidate compound with a variant of the α1 subunit of human AMPK or a plurality of cells expressing a variant of the α1 subunit of human AMPK; and (ii) measuring the effect of the candidate compound on the activation of the variant of the α1 subunit of human AMPK. Modulation of the activation of a variant of the α1 subunit of human AMPK can either increase or decrease the activation. Agents capable of increasing the activation of a variant of the α1 subunit of human AMPK are particularly useful.

Assays used to determine the effect of a compound to be tested on the activity or activation of a variant of the α1 subunit of human AMPK can be based on measurement of the in vitro phosphorylation by AMPK of synthetic peptide substrates as described, for example, by Davies et al. (*Eur. J. Biochem.* 186:123–128, 1989) and Michell et al. (*J. Biol. Chem.* 271:28445–28450, 1996).

Therapeutic agents that can modulate the amount of a variant of the α1 subunit of human AMPK produced by a cell also can be identified using methods of the invention. For example, a candidate compound can be contacted with a plurality of cells expressing a variant of the α1 subunit of human AMPK and the effect of the candidate compound on the amount of the variant of the α1 subunit of human AMPK that is produced by the plurality of cells can be measured. Modulation of the amount of a variant of the α1 subunit of human AMPK that is produced includes increasing or decreasing the amount of the polypeptide that is produced. Therapeutic agents capable of increasing the amount of a variant of the α1 subunit of human AMPK that is produced are particularly useful.

The amount of α1 subunit that is produced in cells can be altered, for example, by modulating transcription, splicing, or translation of nucleic acids encoding the variant of the α1 subunit of human AMPK. Assays used to determine the effect of a test compound on the amount of a variant of the α1 subunit of human AMPK can be based on:

(i) measurement of the amount of mRNA formed using, e.g., Northern blot analysis or quantitative real time PCR, (ii) measurement of the amount of protein formed using, e.g., Western blot analysis, or immunochemical analysis such as ELISA, or (iii) measurement of activity as described above, in cells expressing a variant of the α1 subunit of human AMPK.

Compounds identified by the methods described herein can be used to regulate metabolism. "Regulation of metabolism" as used herein refers to the ability of the therapeutic agent to mediate cell processes related to insulin resistance syndrome and other related disorders, such as non-insulin dependent diabetes mellitus, dyslipidemia, obesity and atherosclerosis.

The invention will be further described in the following examples, which do not limit the scope of the invention described in the claims.

EXAMPLES

Example 1

Materials and Methods

Synthetic oligonucleotides were designed for use as primers to amplify and thus clone the coding region of the α1 catalytic subunit of human AMPK (GenBank accession number NM_006251) by polymerase chain reaction (PCR). The sense primer (AM2sS) with the nucleotide sequence 5'-GAGCATGCAG<u>ATG</u>GCGACAGCCGAGAA-3' (SEQ ID NO:5; start codon underlined) contained a 5' SphI restriction enzyme site and two extra bases on each end, while the anti-sense primer (AM2as) had the nucleotide sequence 5'-TTATTGTGCAAGAATTTTAATTAGAT-3' (SEQ ID NO:6). First strand cDNA was synthesized from human skeletal muscle mRNA (M. quadriceps, iliopsoas, and pectoralis major from male and female; Clontech, Palo Alto, Calif.) using the SuperScript II system (Gibco/Invitrogen, Carlsbad, Calif.). PCR was performed using Advantage 2 polymerase (Clontech), a GenAMP PCR System 9600 instrument (Perkin Elmer, Wellesley, Mass.), and the following cycles: an initial denaturation at 95° C. for one minute; five cycles of 94° C. for 15 seconds, 60° C. for 15 seconds, and 72° C. for 2 minutes; 38 cycles of 94° C. for 15 seconds, 54° C. for 10 seconds, and 72° C. for 2 minutes; and one final segment of 72° C. for 3 minutes. A PCR product approximately 1.7 kb in length was purified from agarose gel. The ends of the PCR product were polished using a T4 DNA polymerase (Amersham Pharmacia Biotech, Piscataway, N.J.) for five minutes at room temperature and thereafter purified using the QIAquick PCR Purification Kit (Qiagen, Valencia, Calif.). The PCR product was digested with SphI (New England BioLabs, Beverly, Mass.) for 90 minutes, after which the cDNA fragment was once again purified. The digested PCR fragment was ligated into the SphI and SmaI sites of the bacterial expression vector pQE-32 (Qiagen) and subsequently transformed into electrocompetent DH10b bacteria (Gibco/Invitrogen). Overnmight cultures were started from individual colonies and mini plasmid preparation was performed using a QIAprep Spin miniprep Kit (Qiagen). DNA sequencing was performed on a MegaBACE 1000 DNA Analysis System (Amersham Biosciences) and DNA sequence analysis was performed using EditView (Applied Biosystems, Foster City, Calif.) and MacVector (Accelrys, Burlington, Mass.) software programs.

Example 2

Identification and Cloning of a Variant of the α1 Subunit of Human AMPK

One of the five clones (SEQ ID NO:3) that were isolated as described in Example 1 contained an internal extra nucleotide sequence of 45 bp, as compared to the published cDNA sequence for the human AMPK α1 subunit (GenBank #NM_006251). These extra 45 bp did not alter the existing reading frame of the α1 subunit of AMPK.

The extra 45 bp correspond to a previously undescribed exon of the human AMPK α1 subunit, when compared to genome clone #AC008810. This new exon adheres to the AG-exon-GT consensus for exon/intron boundaries (International Human Genome Sequencing Consortium, *Nature* 409:860–921, 2001). The corresponding positions in the rat and mouse genes for the AMPK α1 subunit show significant sequence similarity to the human gene, but contain nucleotide substitutions, deletions, and insertions, as well as a lack of consensus motifs at exon/intron boundaries. These differences likely render the corresponding rat and mouse sequences incapable of forming any exon. The rat sequence was found in GenBank #AC094562, and the mouse sequence was obtained by PCR using mouse genomic DNA and AMPK α1 subunit specific primers.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified polypeptide comprising a splice variant of the α1 subunit of human AMP-activated kinase (AMPK) having at least 95% identity to the amino acid sequence of SEQ ID NO:4, and comprising an amino acid sequence having at least 93% identity to the amino acid sequence of SEQ ID NO:2, and wherein said splice variant has kinase activity.

2. The purified polypeptide of claim 1, wherein said polypeptide comprises the amino acid sequence of SEQ ID NO:2.

3. The purified polypeptide of claim 1, wherein said splice variant of the α1 subunit of human AMPK has the amino acid sequence of SEQ ID NO:4.

* * * * *

UNITED STATES PATENT AND TRADEMARK OFFICE
CERTIFICATE OF CORRECTION

| | | |
|---|---|---|
| PATENT NO. | : 7,208,305 B2 | Page 1 of 1 |
| APPLICATION NO. | : 10/503038 | |
| DATED | : April 24, 2007 | |
| INVENTOR(S) | : Göran Hjälm | |

It is certified that error appears in the above-identified patent and that said Letters Patent is hereby corrected as shown below:

Title Page, Item [75] Inventor, please delete "IIjälm" and insert --Hjälm--therefor;

Claim 2 Column 20, line 17, after "said" please insert --purified--.

Signed and Sealed this

Thirty-first Day of July, 2007

JON W. DUDAS
*Director of the United States Patent and Trademark Office*

SEQUENCE LISTING

<160> NUMBER OF SEQ ID NOS: 6

<210> SEQ ID NO 1
<211> LENGTH: 45
<212> TYPE: DNA
<213> ORGANISM: Homo sapiens
<220> FEATURE:
<221> NAME/KEY: exon
<222> LOCATION: (1)..(45)
<223> OTHER INFORMATION:
<220> FEATURE:
<221> NAME/KEY: CDS
<222> LOCATION: (1)..(45)
<223> OTHER INFORMATION:

<400> SEQUENCE: 1

```
aaa tct gat gta cct gga gta gta aaa aca ggc tcc acg aag gag        45
Lys Ser Asp Val Pro Gly Val Val Lys Thr Gly Ser Thr Lys Glu
1               5                   10                  15
```

<210> SEQ ID NO 2
<211> LENGTH: 15
<212> TYPE: PRT
<213> ORGANISM: Homo sapiens

<400> SEQUENCE: 2

```
Lys Ser Asp Val Pro Gly Val Val Lys Thr Gly Ser Thr Lys Glu
1               5                   10                  15
```

<210> SEQ ID NO 3
<211> LENGTH: 1698
<212> TYPE: DNA
<213> ORGANISM: Homo sapiens
<220> FEATURE:
<221> NAME/KEY: CDS
<222> LOCATION: (1)..(1698)
<223> OTHER INFORMATION:

<400> SEQUENCE: 3

```
atg gcg aca gcc gag aag cag aaa cac gac ggg cgg gtg aag atc ggc        48
Met Ala Thr Ala Glu Lys Gln Lys His Asp Gly Arg Val Lys Ile Gly
1               5                   10                  15 cac tac att ctg ggt gac acg ctg ggg gtc ggc acc ttc ggc aaa gtg        96
His Tyr Ile Leu Gly Asp Thr Leu Gly Val Gly Thr Phe Gly Lys Val
                20                  25                  30 aag gtt ggc aaa cat gaa ttg act ggg cat aaa gta gct gtg aag ata       144
Lys Val Gly Lys His Glu Leu Thr Gly His Lys Val Ala Val Lys Ile
            35                  40                  45 ctc aat cga cag aag att cgg agc ctt gat gtg gta gga aaa atc cgc       192
Leu Asn Arg Gln Lys Ile Arg Ser Leu Asp Val Val Gly Lys Ile Arg
        50                  55                  60 aga gaa att cag aac ctc aag ctt ttc agg cat cct cat ata att aaa       240
Arg Glu Ile Gln Asn Leu Lys Leu Phe Arg His Pro His Ile Ile Lys
65                  70                  75                  80 ctg tac cag gtc atc agt aca cca tct gat att ttc atg gtg atg gaa       288
Leu Tyr Gln Val Ile Ser Thr Pro Ser Asp Ile Phe Met Val Met Glu
                85                  90                  95 tat gtc tca gga gga gag cta ttt gat tat atc tgt aag aat gga agg       336
Tyr Val Ser Gly Gly Glu Leu Phe Asp Tyr Ile Cys Lys Asn Gly Arg
                100                 105                 110 aaa tct gat gta cct gga gta gta aaa aca ggc tcc acg aag gag ctg       384
Lys Ser Asp Val Pro Gly Val Val Lys Thr Gly Ser Thr Lys Glu Leu
            115                 120                 125
```

-continued

| | | |
|---|---|---|
| gat gaa aaa gaa agt cgg cgt ctg ttc caa cag atc ctt tct ggt gtg<br>Asp Glu Lys Glu Ser Arg Arg Leu Phe Gln Gln Ile Leu Ser Gly Val<br>130                         135                         140 | | 432 |
| gat tat tgt cac agg cat atg gtg gtc cat aga gat ttg aaa cct gaa<br>Asp Tyr Cys His Arg His Met Val Val His Arg Asp Leu Lys Pro Glu<br>145                         150                         155                        160 | | 480 |
| aat gtc ctg ctt gat gca cac atg aat gca aag ata gct gat ttt ggt<br>Asn Val Leu Leu Asp Ala His Met Asn Ala Lys Ile Ala Asp Phe Gly<br>                         165                         170                        175 | | 528 |
| ctt tca aac atg atg tca gat ggt gaa ttt tta aga aca agt tgt ggc<br>Leu Ser Asn Met Met Ser Asp Gly Glu Phe Leu Arg Thr Ser Cys Gly<br>                   180                         185                        190 | | 576 |
| tca ccc aac tat gct gca cca gaa gta att tca gga aga ttg tat gca<br>Ser Pro Asn Tyr Ala Ala Pro Glu Val Ile Ser Gly Arg Leu Tyr Ala<br>             195                         200                        205 | | 624 |
| ggc cca gag gta gat ata tgg agc agt ggg gtt att ctc tat gct tta<br>Gly Pro Glu Val Asp Ile Trp Ser Ser Gly Val Ile Leu Tyr Ala Leu<br>210                         215                         220 | | 672 |
| tta tgt gga acc ctt cca ttt gat gat gac cat gtg cca act ctt ttt<br>Leu Cys Gly Thr Leu Pro Phe Asp Asp Asp His Val Pro Thr Leu Phe<br>225                         230                         235                        240 | | 720 |
| aag aag ata tgt gat ggg atc ttc tat acc cct caa tat tta aat cct<br>Lys Lys Ile Cys Asp Gly Ile Phe Tyr Thr Pro Gln Tyr Leu Asn Pro<br>                         245                         250                        255 | | 768 |
| tct gtg att agc ctt ttg aaa cat atg ctg cag gtg gat ccc atg aag<br>Ser Val Ile Ser Leu Leu Lys His Met Leu Gln Val Asp Pro Met Lys<br>                   260                         265                        270 | | 816 |
| agg gcc aca atc aaa gat atc agg gaa cat gaa tgg ttt aaa cag gac<br>Arg Ala Thr Ile Lys Asp Ile Arg Glu His Glu Trp Phe Lys Gln Asp<br>             275                         280                        285 | | 864 |
| ctt cca aaa tat ctc ttt cct gag gat cca tca tat agt tca acc atg<br>Leu Pro Lys Tyr Leu Phe Pro Glu Asp Pro Ser Tyr Ser Ser Thr Met<br>290                         295                         300 | | 912 |
| att gat gat gaa gcc tta aaa gaa gta tgt gaa aag ttt gag tgc tca<br>Ile Asp Asp Glu Ala Leu Lys Glu Val Cys Glu Lys Phe Glu Cys Ser<br>305                         310                         315                        320 | | 960 |
| gaa gag gaa gtt ctc agc tgt ctt tac aac aga aat cac cag gat cct<br>Glu Glu Glu Val Leu Ser Cys Leu Tyr Asn Arg Asn His Gln Asp Pro<br>                         325                         330                        335 | | 1008 |
| ttg gca gtt gcc tac cat ctc ata ata gat aac agg aga ata atg aat<br>Leu Ala Val Ala Tyr His Leu Ile Ile Asp Asn Arg Arg Ile Met Asn<br>             340                         345                        350 | | 1056 |
| gaa gcc aaa gat ttc tat ttg gcg aca agc cca cct gat tct ttt ctt<br>Glu Ala Lys Asp Phe Tyr Leu Ala Thr Ser Pro Pro Asp Ser Phe Leu<br>                   355                         360                        365 | | 1104 |
| gat gat cat cac ctg act cgg ccc cat cct gaa aga gta cca ttc ttg<br>Asp Asp His His Leu Thr Arg Pro His Pro Glu Arg Val Pro Phe Leu<br>370                         375                         380 | | 1152 |
| gtt gct gaa aca cca agg gca cgc cat acc ctt gat gaa tta aat cca<br>Val Ala Glu Thr Pro Arg Ala Arg His Thr Leu Asp Glu Leu Asn Pro<br>385                         390                         395                        400 | | 1200 |
| cag aaa tcc aaa cac caa ggt gta agg aaa gca aag tgg cat tta gga<br>Gln Lys Ser Lys His Gln Gly Val Arg Lys Ala Lys Trp His Leu Gly<br>                         405                         410                        415 | | 1248 |
| att aga agt caa agt cga cca aat gat att atg gca gaa gta tgt aga<br>Ile Arg Ser Gln Ser Arg Pro Asn Asp Ile Met Ala Glu Val Cys Arg<br>                   420                         425                        430 | | 1296 |
| gca atc aaa caa ttg gat tat gaa tgg aag gtt gta aac cca tat tat<br>Ala Ile Lys Gln Leu Asp Tyr Glu Trp Lys Val Val Asn Pro Tyr Tyr<br>             435                         440                        445 | | 1344 |

```
ttg cgt gta cga agg aag aat cct gtg aca agc act tac tcc aaa atg       1392
Leu Arg Val Arg Arg Lys Asn Pro Val Thr Ser Thr Tyr Ser Lys Met
450                 455                 460 agt cta cag tta tac caa gtg gat agt aga act tat cta ctg gat ttc       1440
Ser Leu Gln Leu Tyr Gln Val Asp Ser Arg Thr Tyr Leu Leu Asp Phe
465                 470                 475                 480 cgt agt att gat gat gaa att aca gaa gcc aaa tca ggg act gct act       1488
Arg Ser Ile Asp Asp Glu Ile Thr Glu Ala Lys Ser Gly Thr Ala Thr
                485                 490                 495 cca cag aga tcg gga tca gtt agc aac tat cga tct tgc caa agg agt       1536
Pro Gln Arg Ser Gly Ser Val Ser Asn Tyr Arg Ser Cys Gln Arg Ser
        500                 505                 510 gat tca gat gct gag gct caa gga aaa tcc tca gaa gtt tct ctt acc       1584
Asp Ser Asp Ala Glu Ala Gln Gly Lys Ser Ser Glu Val Ser Leu Thr
    515                 520                 525 tca tct gtg acc tca ctt gac tct tct cct gtt gac cta act cca aga       1632
Ser Ser Val Thr Ser Leu Asp Ser Ser Pro Val Asp Leu Thr Pro Arg
530                 535                 540 cct gga agt cac aca ata gaa ttt ttt gag atg tgt gca aat cta att       1680
Pro Gly Ser His Thr Ile Glu Phe Phe Glu Met Cys Ala Asn Leu Ile
545                 550                 555                 560 aaa att ctt gca caa taa                                                1698
Lys Ile Leu Ala Gln
            565
```

<210> SEQ ID NO 4
<211> LENGTH: 565
<212> TYPE: PRT
<213> ORGANISM: Homo sapiens

<400> SEQUENCE: 4

```
Met Ala Thr Ala Glu Lys Gln Lys His Asp Gly Arg Val Lys Ile Gly
1               5                   10                  15

His Tyr Ile Leu Gly Asp Thr Leu Gly Val Gly Thr Phe Gly Lys Val
            20                  25                  30

Lys Val Gly Lys His Glu Leu Thr Gly His Lys Val Ala Val Lys Ile
        35                  40                  45

Leu Asn Arg Gln Lys Ile Arg Ser Leu Asp Val Val Gly Lys Ile Arg
    50                  55                  60

Arg Glu Ile Gln Asn Leu Lys Leu Phe Arg His Pro His Ile Ile Lys
65                  70                  75                  80

Leu Tyr Gln Val Ile Ser Thr Pro Ser Asp Ile Phe Met Val Met Glu
                85                  90                  95

Tyr Val Ser Gly Gly Glu Leu Phe Asp Tyr Ile Cys Lys Asn Gly Arg
            100                 105                 110

Lys Ser Asp Val Pro Gly Val Val Lys Thr Gly Ser Thr Lys Glu Leu
        115                 120                 125

Asp Glu Lys Glu Ser Arg Arg Leu Phe Gln Gln Ile Leu Ser Gly Val
    130                 135                 140

Asp Tyr Cys His Arg His Met Val Val His Arg Asp Leu Lys Pro Glu
145                 150                 155                 160

Asn Val Leu Leu Asp Ala His Met Asn Ala Lys Ile Ala Asp Phe Gly
                165                 170                 175

Leu Ser Asn Met Met Ser Asp Gly Glu Phe Leu Arg Thr Ser Cys Gly
            180                 185                 190

Ser Pro Asn Tyr Ala Ala Pro Glu Val Ile Ser Gly Arg Leu Tyr Ala
        195                 200                 205
```

```
Gly Pro Glu Val Asp Ile Trp Ser Ser Gly Val Ile Leu Tyr Ala Leu
            210                 215                 220

Leu Cys Gly Thr Leu Pro Phe Asp Asp His Val Pro Thr Leu Phe
225                 230                 235                 240

Lys Lys Ile Cys Asp Gly Ile Phe Tyr Thr Pro Gln Tyr Leu Asn Pro
                245                 250                 255

Ser Val Ile Ser Leu Leu Lys His Met Leu Gln Val Asp Pro Met Lys
                260                 265                 270

Arg Ala Thr Ile Lys Asp Ile Arg Glu His Glu Trp Phe Lys Gln Asp
            275                 280                 285

Leu Pro Lys Tyr Leu Phe Pro Glu Asp Pro Ser Tyr Ser Ser Thr Met
290                 295                 300

Ile Asp Asp Glu Ala Leu Lys Glu Val Cys Glu Lys Phe Glu Cys Ser
305                 310                 315                 320

Glu Glu Glu Val Leu Ser Cys Leu Tyr Asn Arg Asn His Gln Asp Pro
                325                 330                 335

Leu Ala Val Ala Tyr His Leu Ile Ile Asp Asn Arg Arg Ile Met Asn
                340                 345                 350

Glu Ala Lys Asp Phe Tyr Leu Ala Thr Ser Pro Pro Asp Ser Phe Leu
            355                 360                 365

Asp Asp His His Leu Thr Arg Pro His Pro Glu Arg Val Pro Phe Leu
370                 375                 380

Val Ala Glu Thr Pro Arg Ala Arg His Thr Leu Asp Glu Leu Asn Pro
385                 390                 395                 400

Gln Lys Ser Lys His Gln Gly Val Arg Lys Ala Lys Trp His Leu Gly
                405                 410                 415

Ile Arg Ser Gln Ser Arg Pro Asn Asp Ile Met Ala Glu Val Cys Arg
                420                 425                 430

Ala Ile Lys Gln Leu Asp Tyr Glu Trp Lys Val Val Asn Pro Tyr Tyr
            435                 440                 445

Leu Arg Val Arg Arg Lys Asn Pro Val Thr Ser Thr Tyr Ser Lys Met
450                 455                 460

Ser Leu Gln Leu Tyr Gln Val Asp Ser Arg Thr Tyr Leu Leu Asp Phe
465                 470                 475                 480

Arg Ser Ile Asp Asp Glu Ile Thr Glu Ala Lys Ser Gly Thr Ala Thr
                485                 490                 495

Pro Gln Arg Ser Gly Ser Val Ser Asn Tyr Arg Ser Cys Gln Arg Ser
                500                 505                 510

Asp Ser Asp Ala Glu Ala Gln Gly Lys Ser Ser Glu Val Ser Leu Thr
            515                 520                 525

Ser Ser Val Thr Ser Leu Asp Ser Ser Pro Val Asp Leu Thr Pro Arg
530                 535                 540

Pro Gly Ser His Thr Ile Glu Phe Phe Glu Met Cys Ala Asn Leu Ile
545                 550                 555                 560

Lys Ile Leu Ala Gln
                565
```

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5

```
gagcatgcag atggcgacag ccgagaa                                               27

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
ttattgtgca agaattttaa ttagat                                                26
```